(12) United States Patent
Nisbet et al.

(10) Patent No.: US 8,530,606 B2
(45) Date of Patent: Sep. 10, 2013

(54) PROCESS FOR PREPARING DIARYL CARBONATES

(75) Inventors: Timothy Michael Nisbet, Amsterdam (NL); Garo Garbis Vaporciyan, Houston, TX (US); Cornelis Leonardus Maria Vrouwenvelder, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/513,214

(22) PCT Filed: Nov. 30, 2010

(86) PCT No.: PCT/EP2010/068568
§ 371 (c)(1),
(2), (4) Date: Jun. 1, 2012

(87) PCT Pub. No.: WO2011/067263
PCT Pub. Date: Jun. 9, 2011

(65) Prior Publication Data
US 2012/0245319 A1    Sep. 27, 2012

(30) Foreign Application Priority Data

Dec. 4, 2009 (EP) .................................... 09177993

(51) Int. Cl.
*C08G 64/00* (2006.01)
*C08G 63/02* (2006.01)

(52) U.S. Cl.
USPC ........... 528/196; 202/153; 202/158; 422/610; 528/198; 558/270; 558/274

(58) Field of Classification Search
USPC ................. 202/153, 158; 422/610; 558/270, 558/274
See application file for complete search history.

(56) References Cited

U.S. PATENT DOCUMENTS 6,294,684 B1 * 9/2001 de Bruin et al. .............. 558/274

FOREIGN PATENT DOCUMENTS

| EP | 2036880 | 3/2009 |
| EP | 2135857 | 12/2009 |
| WO | WO0142187 | 6/2001 |

* cited by examiner

Primary Examiner — Terressa Boykin

(57) ABSTRACT

The invention relates to a process for preparing a diaryl carbonate from a dialkyl carbonate and an aryl alcohol using a series of reactive distillation columns.

12 Claims, 2 Drawing Sheets

US 8,530,606 B2

PROCESS FOR PREPARING DIARYL CARBONATES

PRIORITY CLAIM

The present application claims priority from PCT/EP2010/068568, filed 30 Nov. 2010, which claims priority from EP 09177993.4, filed 4 Dec. 2009.

FIELD OF INVENTION

The present invention relates to a process for preparing a diaryl carbonate from a dialkyl carbonate and an aryl alcohol

BACKGROUND

In such processes, the dialkyl carbonate is converted into diaryl carbonate via the following steps. In a first step transesterification of the dialkyl carbonate with the aryl alcohol takes place to yield alkyl aryl carbonate and alkyl alcohol. In a second step disproportionation of the alkyl aryl carbonate takes place to yield diaryl carbonate and dialkyl carbonate. Further transesterification of the alkyl aryl carbonate with aryl alcohol yielding diaryl carbonate and alkyl alcohol may also take place.

WO200142187 discloses a process for preparing diphenyl carbonate from a dialkyl carbonate and phenol. In said process, use is made of 3 reactive distillation columns in series: see columns A, B1 and C in FIG. 2 of WO200142187. Said process is characterized in that the top stream from the third reactive distillation column C is recycled to the first reactive distillation column A.

SUMMARY OF THE INVENTION

It is an object of the present invention to provide a process for preparing a diaryl carbonate from a dialkyl carbonate and an aryl alcohol, wherein the energy required to make that diaryl carbonate is reduced.

Surprisingly, it was found that such energy efficient preparation of diaryl carbonate can be achieved in a process using three reactive distillation columns in series, in which process the top stream from the third reactive distillation column is recycled to the second reactive distillation column.

Accordingly, the present invention relates to a process for preparing a diaryl carbonate from a dialkyl carbonate and an aryl alcohol comprising:
(a) introducing dialkyl carbonate and aryl alcohol into a first reactive distillation column;
(b) recovering from the first reactive distillation column a top stream comprising dialkyl carbonate and alkyl alcohol and a bottom stream comprising alkyl aryl carbonate, aryl alcohol and dialkyl carbonate;
ok(c) introducing the bottom stream from the first reactive distillation column into a second reactive distillation column;
(d) recovering from the second reactive distillation column a top stream comprising dialkyl carbonate and a bottom stream comprising alkyl aryl carbonate, diaryl carbonate and aryl alcohol;
(e) introducing the bottom stream from the second reactive distillation column into a third reactive distillation column; and
(f) recovering from the third reactive distillation column a top stream comprising aryl alcohol and a bottom stream comprising diaryl carbonate,
wherein the top stream from the third reactive distillation column is recycled to the second reactive distillation column.

DETAILED DESCRIPTION OF THE INVENTION

Figure 1:
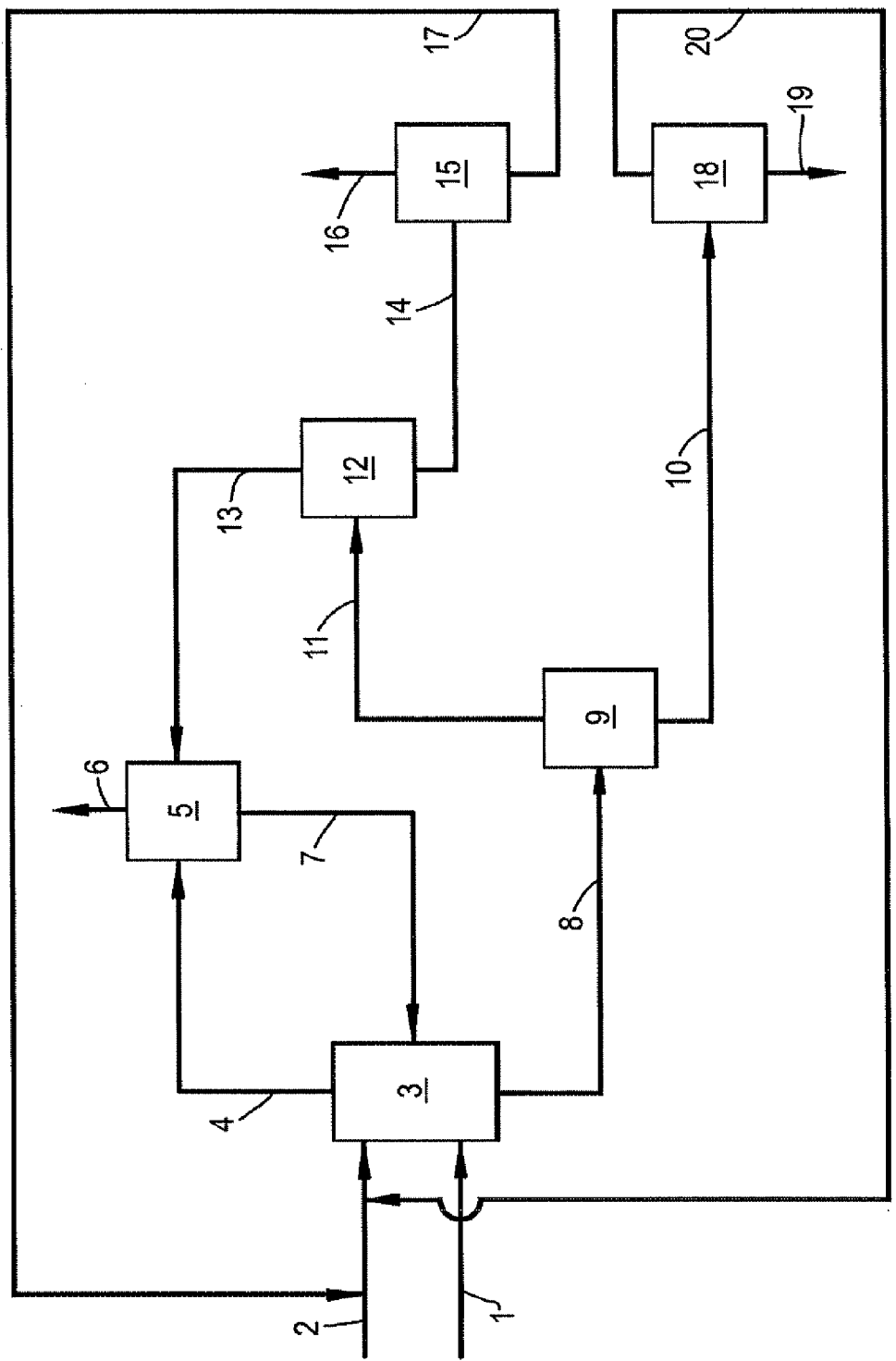
FIG. 1 exemplifies a prior art process.

The present invention advantageously results in less stringent energy requirements for preparing a diaryl carbonate from a dialkyl carbonate and an aryl alcohol, as is shown in the Examples below.

In the present specification, a "reactive distillation column" is defined as a distillation column containing a catalyst for effecting a chemical reaction in the distillation column.

Preferably, the top stream from the first reactive distillation column is introduced into a first distillation column from which a top stream comprising alkyl alcohol and a bottom stream comprising dialkyl carbonate are recovered, and the bottom stream from the first distillation column is recycled to the first reactive distillation column.

Further, preferably, the top stream comprising dialkyl carbonate from the second reactive distillation column additionally comprises aryl alcohol and is introduced into a second distillation column from which a top stream comprising dialkyl carbonate and a bottom stream comprising aryl alcohol are recovered, and the top stream from the second distillation column is recycled to the first distillation column.

Still further, preferably, the bottom stream from the first reactive distillation column, the top stream from the second reactive distillation column and the bottom stream comprising aryl alcohol from the second distillation column additionally comprise alkyl aryl ether, the bottom stream comprising aryl alcohol and alkyl aryl ether from the second distillation column is introduced into a third distillation column from which a top stream comprising alkyl aryl ether and a bottom stream comprising aryl alcohol are recovered, and the bottom stream from the third distillation column is recycled to the first reactive distillation column.

The bottom stream from the third reactive distillation column comprises the desired diaryl carbonate. Said stream may be subjected to further distillation to obtain pure diaryl carbonate. In a case where the stream comprising diaryl carbonate from the third reactive distillation column additionally comprises catalyst, said stream is introduced into a fourth distillation column from which a top stream comprising diaryl carbonate and a bottom stream comprising catalyst and diaryl carbonate are recovered. The bottom stream from the fourth distillation column may be partially or completely recycled to the first, second or third reactive distillation column.

The dialkyl carbonate to be used in the present invention may be a di($C_1$-$C_5$)alkyl carbonate, wherein the alkyl groups (straight, branched and/or cyclic) may be the same or different, such as methyl, ethyl and propyl. Suitable dialkyl carbonates are dimethyl carbonate and diethyl carbonate. Preferably the dialkyl carbonate is diethyl carbonate.

The aryl alcohol to be used in the present invention is selected from unsubstituted phenol or mono-, di- or tri-substituted phenol. The substituents on the phenyl moiety can be selected from a wide range of organic groups. Suitable substituents include $C_1$-$C_4$ alkyl groups, $C_1$-$C_4$ alkoxy groups, and halides. Examples are methyl, ethyl, methoxy and ethoxy groups. The substituents can be present on any position in the ring. Hence, suitable substituted phenol compounds include o-, m- or p-cresol, o-, m- or p-ethyl phenol, o-, m- or p-chlorophenol, o-, m- or p-methoxy phenol, 2,3-, 2,4- or 3,4-dimethyl phenol. Preferably the aryl alcohol is unsubstituted phenol.

As mentioned above, the first, second and third reactive distillation columns contain a catalyst for effecting a chemical reaction in the distillation column. Said catalyst may be homogeneous or heterogeneous.

The selection of the catalyst to be used in the first, second and third reactive distillation columns of the present process is not critical. The catalysts to be used in the first, second and third reactive distillation columns need not be the same. Many catalysts for transesterification of diaryl carbonate, and possibly alkyl aryl arbonate, with aryl alcohol and for disproportionation of alkyl aryl arbonate are known in prior art. Suitable catalysts include oxides, hydroxides, alcoholates, amides and hydrides of alkali and alkaline earth metals. Salts of alkali metals or alkaline earth metals include alkali metal carboxylates, carbonates and bicarbonates. The metal is preferably selected from sodium, potassium, magnesium and calcium, sodium and potassium being specifically preferred. Preferred catalysts are alkali metal hydroxides, such as sodium or potassium hydroxide, and alcoholates, such as sodium or potassium methanolate or ethanolate.

Further catalysts can be Lewis acid metal compounds, such as $AlX_2$, $TiX_3$, $TiX_4$, $VX_5$, $ZnX_2$, $FeX_3$ and $SnX_4$. For a specific compound having one of the aforementioned formulas, X may be the same or different. Further, said X may be selected from the group consisting of hydrogen, acetoxy, alkoxy, arylalkoxy and aryloxy groups. Preferably, the catalyst is a homogeneous catalyst of formula $TiX_4$ wherein X may be the same or different and is selected from an alkoxy group, preferably an alkoxy group containing from 1 to 6 carbon atoms, more preferably an ethoxy group, and an aryloxy group, preferably a phenoxy group. Other suitable examples are titanium tetramethoxide, titanium dimethoxide, titanium diethoxide, titanium tetrapropoxide, and titanium tetrabutoxide. The alkoxide group can be linear or branched wherein linear alkoxide groups are preferred.

Thus, specifically, the transesterification catalyst is a titanium containing catalyst. Preferably, the titanium in said titanium containing catalyst has an oxidation state of IV. Further, said titanium may be bonded to one or more, preferably four, alkoxide groups, such as ethoxide groups, and/or aryloxide groups, such as phenoxide groups.

Further, the above-mentioned titanium containing catalyst may be a dimer or polymer containing 2 or more titanium atoms, wherein titanium atoms may be bonded to each other via a carbonate bridge of formula —O(C=O)O— or via an oxygen bridge of formula —O—. Still further, said titanium containing catalyst may additionally contain one or more silicon atoms wherein the titanium and silicon atoms are bonded to each other via an oxygen bridge of formula —O—.

Another type of suitable catalysts includes lead compounds comprising carbonate, carboxylate, hydroxide and phosphine groups. Examples are lead acetate and lead carbonate.

Combinations of the above types of catalysts are also possible. Heterogeneous catalysts are also suitable. Examples of suitable heterogeneous catalysts include mixed oxides of silicon and titanium and titanium dioxides. A preferred heterogeneous catalyst is one wherein titanium is immobilised on silica.

Still further, a combination of heterogeneous and homogeneous catalysts may be used in any one of the first, second and third distillation columns.

The catalyst may be introduced into the first distillation column together with one or more of the reactants. Preferably, the aryl alcohol is introduced into the first reactive distillation column at a point which is higher than the point of introduction of the dialkyl carbonate, as in such way counter-currents are created wherein the aryl alcohol (preferably phenol) moves downward and the dialkyl carbonate (preferably dimethyl carbonate or diethyl carbonate) moves upward thereby increasing reaction efficiency. In such case, the catalyst is preferably introduced into the first reactive distillation column together with the aryl alcohol. Alternatively or additionally, the first reactive distillation column may be provided with a heterogeneous catalyst which stays inside the column, for example between the point of introduction of the aryl alcohol and the point of introduction of the dialkyl carbonate.

Further, in case the bottom stream from the first reactive distillation column comprises catalyst, for example a homogeneous catalyst, no additional catalyst needs to be introduced into the second and/or third reactive distillation columns.

Minor amounts of catalyst may be used in the present invention. In general the concentrations of catalyst, for example a homogeneous catalyst, may vary from 0.001 to 2% wt, based on total weight of the mixture containing the catalyst. Preferred concentrations include 0.005 to 1% wt, more preferred concentrations being from 0.01 to 0.5% wt.

The pressures in the three reactive distillation columns may vary within wide limits. The pressure at the top of the first reactive distillation column may be 2 to 7 bar, preferably 2.5 to 5 bar. The pressure at the top of the second reactive distillation column may be 0.1 to 3 bar, preferably 0.3 to 1.5 bar. The pressure at the top of the third reactive distillation column may be 10 to 400 mbar, preferably 20 to 200 mbar. Preferably, the pressure at the top of the first reactive distillation column is higher than that of the second reactive distillation column which in turn is higher than that of the third reactive distillation column.

The temperatures in the three reactive distillation columns may also vary within wide limits. The temperature at the bottom of the first, second and third reactive distillation columns may be 50 to 350° C., preferably 120 to 280° C., more preferably 150 to 250° C., most preferably 160 to 240° C.

The diaryl carbonate produced in the process of the present invention is suitably used in the preparation of polycarbonates by the polymerisation with a dihydroxy aromatic compound, preferably with bisphenol A which is 4,4'-(propan-2-ylidene)diphenol. Accordingly, the present invention also relates to a process for making a polycarbonate, comprising reacting a dihydroxy aromatic compound with a diaryl carbonate prepared in accordance with the process as described above. Further, the present invention also relates to a process for making a polycarbonate, comprising preparing a diaryl carbonate in accordance with the process as described above, and reacting a dihydroxy aromatic compound with the diaryl carbonate thus obtained.

Figure 2:
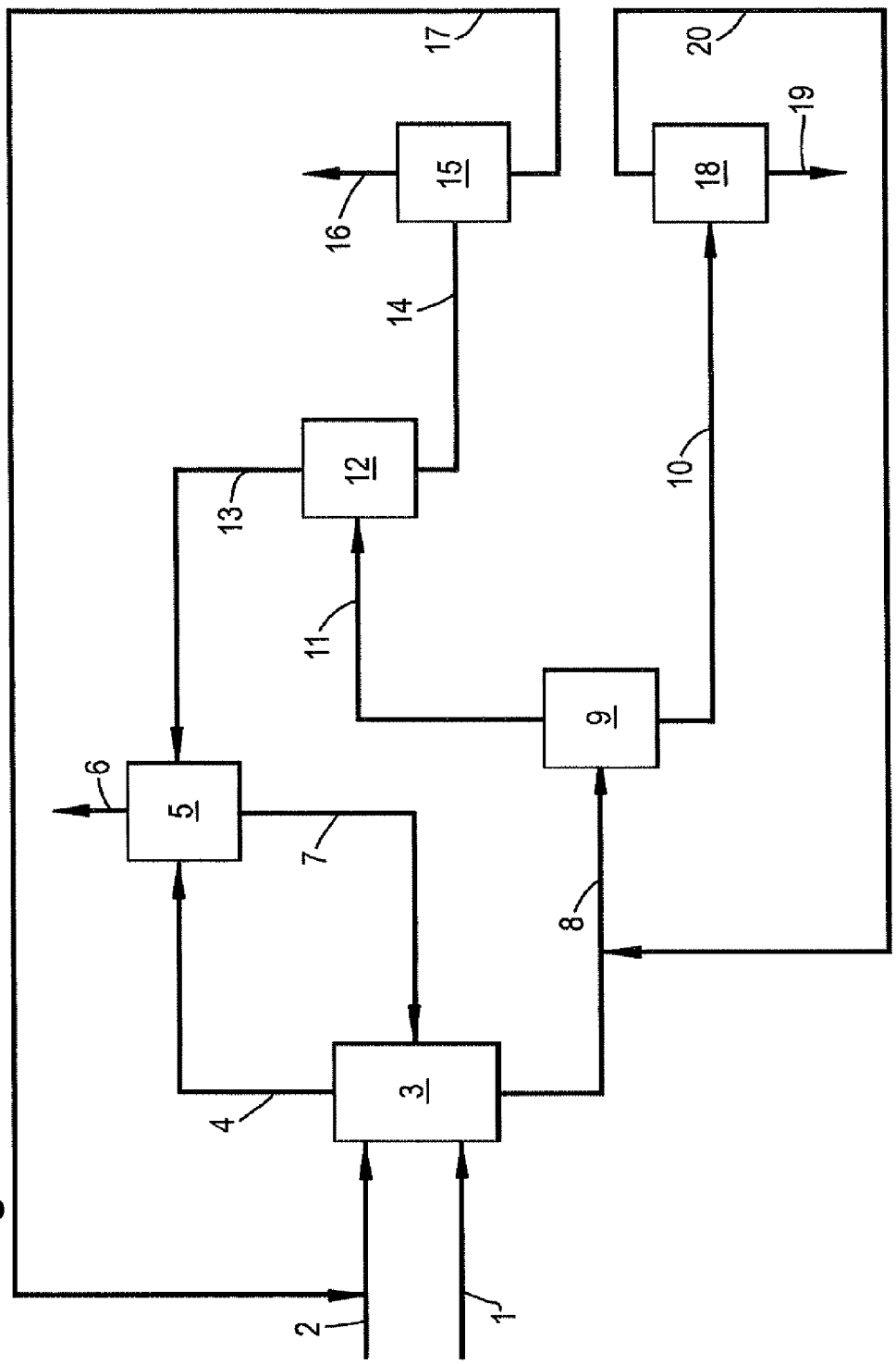
FIG. 2 exemplifies a process according to the present invention.

The set-up as shown in FIG. 2 exemplifies the present invention and may be used to produce diphenyl carbonate (DPC) from diethyl carbonate (DEC) and phenol in three reactive distillion columns 3, 9 and 18, wherein the top stream from third reactive distillation column 18 is recycled to second reactive distillation column 9, as further described below.

The set-up as shown in FIG. 1 exemplifies a prior art process as for example described in above-mentioned WO200142187, and may be used to produce DPC from DEC and phenol in three reactive distillion columns 3, 9 and 18, wherein the top stream from third reactive distillation column 18 is recycled to first reactive distillation column 3, as further described below.

In the set-ups of FIGS. 1 and 2, diethyl carbonate is continuously passed via line 1 into first reactive distillation column 3. Via line 2 phenol is also continuously fed into first reactive distillation column 3.

A mixture comprising DEC, ethanol and phenol is withdrawn from first reactive distillation column 3 via line 4. Said mixture is passed to distillation column 5 where it is separated into a top fraction comprising ethanol and DEC that is withdrawn via line 6 and a bottom fraction comprising DEC and phenol that is recycled to first reactive distillation column 3 via line 7.

A mixture comprising phenol, DEC, ethyl phenyl carbonate (EPC), ethyl phenyl ether (EPE) and DPC is withdrawn from first reactive distillation column 3 via line 8. Said mixture is then passed to second reactive distillation column 9 where it is separated into a top fraction and a bottom fraction. The top fraction comprises DEC, phenol, EPC, EPE and ethanol and is sent to distillation column 12 via line 11. The bottom fraction comprises DPC, EPC, phenol, DEC and EPE and is sent to third reactive distillation column 18 via line 10.

In distillation column 12, a separation takes place into a top fraction comprising DEC and ethanol and a bottom fraction comprising phenol, EPE and EPC. The top fraction is sent to distillation column 5 via line 13. The bottom fraction is sent to distillation column 15 via line 14 and separated into a top fraction comprising phenol and EPE and withdrawn via line 16 and a bottom fraction comprising phenol, EPE and EPC and recycled to first reactive distillation column 3 via lines 17 and 2 consecutively.

In third reactive distillation column 18, a separation takes place into a top fraction comprising phenol, DEC and EPC and withdrawn via line 20 and a bottom fraction comprising DPC and withdrawn via line 19.

In the set-up of FIG. 1 (prior art), the top stream from third reactive distillation column 18 in line 20 is recycled to first reactive distillation column 3 via line 2, whereas in the set-up of FIG. 2 (present invention) said stream is recycled to second reactive distillation column 9 via line 8.

The invention is further illustrated by the following Examples.

Example and Comparative Example

In the Example exemplifying the invention, the set-up as shown in FIG. 2 is used to produce diphenyl carbonate (DPC) from diethyl carbonate (DEC) and phenol. In the Comparative Example exemplifying a prior art process as for example described in WO200142187, the set-up as shown in FIG. 1 is used to also produce DPC from DEC and phenol.

In the Example and the Comparative Example, DEC is continuously passed via line 1 into first reactive distillation column 3. Via line 2 phenol is also continuously fed into first reactive distillation column 3.

A top fraction is withdrawn from first reactive distillation column 3 via line 4. Said top fraction is passed to distillation column 5 where it is separated into a top fraction that is withdrawn via line 6 and a bottom fraction that is recycled to first reactive distillation column 3 via line 7.

A bottom fraction is withdrawn from first reactive distillation column 3 via line 8. Said bottom fraction is then passed to second reactive distillation column 9 where it is separated into a top fraction and a bottom fraction. The top fraction is sent to distillation column 12 via line 11. The bottom fraction is sent to third reactive distillation column 18 via line 10.

In distillation column 12, a separation takes place into a top fraction and a bottom fraction. The top fraction is sent to distillation column 5 via line 13. The bottom fraction is sent to distillation column 15 via line 14 and separated into a top fraction that is withdrawn via line 16 and a bottom fraction that is recycled to first reactive distillation column 3 via lines 17 and 2 consecutively.

In third reactive distillation column 18, a separation takes place into a top fraction that is withdrawn via line 20 and a bottom fraction that is withdrawn via line 19.

In the Comparative Example the top stream from third reactive distillation column 18 in line 20 is recycled to first reactive distillation column 3 via line 2, whereas in the Example said stream is recycled to second reactive distillation column 9 via line 8.

In Table 1 below, a few characteristics for columns 3, 5, 9, 12, 15 and 18 used in the Example and Comparative Example are mentioned.

In Tables 2 and 3 below, the following parameters are provided for the streams from the Comparative Example (Table 2) and the Example (Table 3) as present in lines 1, 2, 4, 6, 7, 8, 10, 11, 13, 14, 16, 17, 19 and 20 as indicated in FIG. 1 and FIG. 2, respectively: components of the streams, total mass flow and the mass flow per component of the stream. All streams are liquid. Flows are given to the nearest kg/h.

As shown in Tables 2 and 3, in both the Example and the Comparative Example (see line 19), the DPC production rate is 60 kg/h. As mentioned above, the only difference between the set-ups used in the Example and the Comparative Example is that in the Comparative Example the stream in line 20 is recycled to first reactive distillation column 3, whereas in the Example said same stream is recycled to second reactive distillation column 9. It appears that the total heating duty in the Comparative Example is 193 kW, whereas the total heating duty in the Example is advantageously only 178 kW.

TABLE 1

| Column no. in FIG. 1 and 2 | Total number of theoretical stages | Stage at which feed is let in (1) | Condenser pressure (bara) | Reboiler temperature (° C.) | Reflux ratio (R/D) |
|---|---|---|---|---|---|
| 3 | 24 | 8 (streams in lines 2, 17 and 20) (2) 24 (streams in lines 1 and 7) | 3 | 210 | 1.0 |
| 5 | 25 | 21 | 2.1 | 157 | 3.9 |
| 9 | 8 | 4 | 0.6 | 220 | 0.3 |
| 12 | 18 | 4 | 1.5 | 204 | 1.2 |
| 15 | 20 | 15 | 1.5 | 201 | 20 |
| 18 | 10 | 3 | 0.05 | 222 | 0.1 |

(1) The condenser of the column is represented by stage no. 1.
(2) Stream 20 only in Comparative Example.

TABLE 2

| | line | | | | | | | | | | | | | |
|---|---|---|---|---|---|---|---|---|---|---|---|---|---|---|
| | 1 | 2 | 4 | 6 | 7 | 8 | 10 | 11 | 13 | 14 | 16 | 17 | 19 | 20 |
| TMF | 38 | 59 | 226 | 28 | 336 | 361 | 93 | 268 | 138 | 130 | 3 | 127 | 66 | 27 |
| MF DEC | 38 | | 164 | 1 | 299 | 113 | | 136 | 136 | | | | | 2 |
| MF PhOH | | 59 | 35 | | 35 | 141 | 17 | 121 | | 121 | 1 | 119 | 2 | 15 |
| MF EtOH | | | 25 | 27 | | | | 2 | 2 | | | | | |
| MF EPC | | | | | | 93 | 15 | 5 | | 5 | | 5 | 3 | 8 |
| MF DPC | | | | | | 10 | 60 | | | | | | 60 | 2 |
| MF others | | | 2 | | 2 | 4 | 1 | 4 | | 4 | 2 | 3 | 1 | |

Explanation:
TMF = total mass flow (kg/h);
MF = mass flow (kg/h);
DEC = diethyl carbonate;
PhOH = phenol;
EtOH = ethanol;
EPC = ethyl phenyl carbonate;
DPC = diphenyl carbonate;
Others = other compounds in the process.

TABLE 3

| | line | | | | | | | | | | | | | |
|---|---|---|---|---|---|---|---|---|---|---|---|---|---|---|
| | 1 | 2 | 4 | 6 | 7 | 8 | 10 | 11 | 13 | 14 | 16 | 17 | 19 | 20 |
| TMF | 38 | 59 | 420 | 28 | 477 | 223 | 95 | 129 | 85 | 44 | 3 | 40 | 66 | 29 |
| MF DEC | 38 | | 391 | 1 | 474 | 62 | | 85 | 84 | | | | | 2 |
| MF PhOH | | 59 | 3 | | 3 | 54 | 16 | 37 | | 37 | 1 | 35 | 2 | 14 |
| MF EtOH | | | 26 | 27 | | | | 1 | 1 | | | | | |
| MF EPC | | | | | | 89 | 19 | 5 | | 5 | | 5 | 3 | 10 |
| MF DPC | | | | | | 15 | 59 | | | | | | 60 | 2 |
| MF others | | | | | | 4 | 1 | 1 | | 2 | 2 | | 1 | 1 |

Explanation:
TMF = total mass flow (kg/h);
MF = mass flow (kg/h);
DEC = diethyl carbonate;
PhOH = phenol;
EtOH = ethanol;
EPC = ethyl phenyl carbonate;
DPC = diphenyl carbonate;
Others = other compounds in the process.

What is claimed is:

1. A process for preparing a diaryl carbonate from a dialkyl carbonate and an aryl alcohol comprising:
   (a) introducing dialkyl carbonate and aryl alcohol into a first reactive distillation column;
   (b) recovering from the first reactive distillation column a top stream comprising dialkyl carbonate and alkyl alcohol and a bottom stream comprising alkyl aryl carbonate, aryl alcohol and dialkyl carbonate;
   (c) introducing the bottom stream from the first reactive distillation column into a second reactive distillation column;
   (d) recovering from the second reactive distillation column a top stream comprising dialkyl carbonate and a bottom stream comprising alkyl aryl carbonate, diaryl carbonate and aryl alcohol;
   (e) introducing the bottom stream from the second reactive distillation column into a third reactive distillation column; and
   (f) recovering from the third reactive distillation column a top stream comprising aryl alcohol and a bottom stream comprising diaryl carbonate,
   wherein the top stream from the third reactive distillation column is recycled to the second reactive distillation column.

2. A process according to claim 1, wherein the pressure at the top of the first reactive distillation column is higher than that of the second reactive distillation column which in turn is higher than that of the third reactive distillation column.

3. A process according to claim 1, wherein the pressure at the top of the first reactive distillation column is 2 to 7 bar; the pressure at the top of the second reactive distillation column is 0.1 to 3 bar; and the pressure at the top of the third reactive distillation column is 10 to 400 mbar.

4. A process according to claim 1, wherein the top stream from the first reactive distillation column is introduced into a first distillation column from which a top stream comprising alkyl alcohol and a bottom stream comprising dialkyl carbonate are recovered, and the bottom stream from the first distillation column is recycled to the first reactive distillation column.

5. A process according to claim 4, wherein the top stream comprising dialkyl carbonate from the second reactive distillation column additionally comprises aryl alcohol and is introduced into a second distillation column from which a top stream comprising dialkyl carbonate and a bottom stream comprising aryl alcohol are recovered, and the top stream from the second distillation column is recycled to the first distillation column.

6. A process according to claim 5, wherein the bottom stream from the first reactive distillation column, the top stream from the second reactive distillation column and the bottom stream comprising aryl alcohol from the second distillation column additionally comprise alkyl aryl ether, the bottom stream comprising aryl alcohol and alkyl aryl ether from the second distillation column is introduced into a third distillation column from which a top stream comprising alkyl aryl ether and a bottom stream comprising aryl alcohol are recovered, and the bottom stream from the third distillation column is recycled to the first reactive distillation column.

7. A process according to claim 1, wherein the dialkyl carbonate is a di($C_1$-$C_5$)alkyl carbonate, such as dimethyl carbonate or diethyl carbonate.

8. A process according to claim 1, wherein the aryl alcohol is phenol.

9. A process for making a polycarbonate, comprising reacting a dihydroxy aromatic compound with a diaryl carbonate prepared in accordance with the process of claim 1.

10. A process for making a polycarbonate, comprising preparing a diaryl carbonate in accordance with the process of claim 1, and reacting a dihydroxy aromatic compound with the diaryl carbonate thus obtained.

11. A process according to claim 9, wherein the dihydroxy aromatic compound is bisphenol A.

12. A process according to claim 10, wherein the dihydroxy aromatic compound is bisphenol A.

* * * * *